(12) United States Patent
Wangen (10) Patent No.: US 11,951,244 B2
(45) Date of Patent: Apr. 9, 2024

(54) FLUID TEMPERATURE CONTROL DEVICE FOR AN EXTRACORPOREAL BLOOD TREATMENT APPARATUS AND EXTRACORPOREAL BLOOD TREATMENT APPARATUS

(71) Applicant: GAMBRO LUNDIA AB, Lund (SE)

(72) Inventor: Michael Jon Wangen, Rogers, MN (US)

(73) Assignee: Gambro Lundia AB, Lund (SE)

( * ) Notice: Subject to any disclaimer, the term of this patent is extended or adjusted under 35 U.S.C. 154(b) by 735 days.

(21) Appl. No.: 17/054,604

(22) PCT Filed: May 10, 2019

(86) PCT No.: PCT/EP2019/062094
§ 371 (c)(1),
(2) Date: Nov. 11, 2020

(87) PCT Pub. No.: WO2019/219544
PCT Pub. Date: Nov. 21, 2019

(65) Prior Publication Data
US 2021/0100944 A1   Apr. 8, 2021

(30) Foreign Application Priority Data
May 14, 2018   (EP) .................................. 18172120

(51) Int. Cl.
*A61M 1/36* (2006.01)
*A61M 1/00* (2006.01)
(Continued)

(52) U.S. Cl.
CPC ............ *A61M 1/369* (2013.01); *A61M 1/166* (2014.02); *A61M 1/1664* (2014.02);
(Continued)

(58) Field of Classification Search
CPC .. A61M 1/166; A61M 1/1664; A61M 1/3653; A61M 1/369; A61M 1/68;
(Continued)

(56) References Cited

U.S. PATENT DOCUMENTS

| | | |
|---|---|---|
| 5,531,697 A | 7/1996 | Olsen |
| 5,644,402 A | 7/1997 | Chevallet |

(Continued)

FOREIGN PATENT DOCUMENTS

| | | |
|---|---|---|
| CN | 200951223 | 9/2007 |
| CN | 102438577 | 5/2012 |

(Continued)

OTHER PUBLICATIONS

Extended European Search Report for Application No. 18172120 dated Nov. 16, 2018 (7 pages).

(Continued)

*Primary Examiner* — John Kim
(74) *Attorney, Agent, or Firm* — Mueting Raasch Group (57) ABSTRACT

A fluid temperature control device for an extracorporeal blood treatment apparatus, comprises: a casing (26) delimiting a heating/cooling seat (20) configured to accommodate a fluid warming bag (17) connected or connectable to an extracorporeal blood treatment apparatus (1); heating elements (29, 30) operatively active in the heating seat (20) to heat the fluid warming bag (17); at least a presence detector (32, 33) operatively active in the heating seat (20) to detect the presence of the fluid warming bag (17). The presence detector (32, 33) comprises an electromagnetic transmitter (34) and an electromagnetic receiver (35). The electromagnetic receiver (35) is positioned with respect to the electromagnetic transmitter (34) either to receive an electromagnetic radiation emitted by the electromagnetic transmitter (34) and reflected by the fluid warming bag (17) only when (Continued)

the fluid warming bag (17) is properly accommodated in the heating seat (20) or only when the fluid warming bag (17) is not properly accommodated in the heating seat (20).

33 Claims, 6 Drawing Sheets

(51) Int. Cl.
  *A61M 1/16* (2006.01)
  *A61M 5/44* (2006.01)
  *A61M 5/46* (2006.01)

(52) U.S. Cl.
  CPC ...... *A61M 1/36223* (2022.05); *A61M 1/3653* (2013.01); *A61M 1/68* (2021.05); *A61M 5/445* (2013.01); *A61M 5/46* (2013.01); *A61M 2205/18* (2013.01); *A61M 2205/3306* (2013.01); *A61M 2205/36* (2013.01); *A61M 2205/6063* (2013.01)

(58) Field of Classification Search
  CPC .... A61M 5/445; A61M 5/46; A61M 2205/18; A61M 2205/3306; A61M 2205/36; A61M 2205/6063
  See application file for complete search history.

(56) References Cited

U.S. PATENT DOCUMENTS

| | | | |
|---|---|---|---|
| 8,673,139 | B2 | 3/2014 | Hedmann |
| 9,987,412 | B2 | 6/2018 | Ahrens |
| 10,302,075 | B2 | 5/2019 | Tracey |
| 2001/0009610 | A1 | 7/2001 | Augustine |
| 2011/0186517 | A1 | 8/2011 | Hedmann |
| 2012/0063973 | A1 | 3/2012 | Ang |
| 2015/0202383 | A1 | 7/2015 | Juretich |

FOREIGN PATENT DOCUMENTS

| | | |
|---|---|---|
| CN | 102802693 | 11/2012 |
| CN | 105561413 | 5/2016 |
| CN | 105939739 A | 9/2016 |
| JP | S61-072545 | 5/1986 |
| JP | S63-104864 | 5/1988 |
| JP | H09-511931 | 12/1997 |
| JP | 2000-093449 | 4/2000 |
| JP | 2009-533154 | 9/2009 |
| WO | WO 2014/126964 | 8/2014 |

OTHER PUBLICATIONS

PCT Search Report and Written Opinion for PCT/EP2019/062094 dated May 10, 2019 (14 pages).
Office Action issued in Japan for Application No. 2020-564067 dated May 9, 2023 (18 pages). English translation included.
Office Action issued in China for Application No. 201980032839.4 dated Dec. 16, 2021 (15 pages).
Office Action issued in China for Application No. 201980032839.4 dated Oct. 8, 2022 (45 pages). English translation included.

FLUID TEMPERATURE CONTROL DEVICE FOR AN EXTRACORPOREAL BLOOD TREATMENT APPARATUS AND EXTRACORPOREAL BLOOD TREATMENT APPARATUS

This application is a U.S. National Stage Application of International Application No. PCT/EP2019/062094, filed May 10, 2019, which was published in English on Nov. 21, 2019 as International Publication No. WO 2019/219544 A1. International Application No. PCT/EP2019/062094 claims priority to European Application No. 18172120.0 filed May 14, 2018.

FIELD OF THE INVENTION

The present invention relates to a fluid temperature control device (e.g. a warming device) for an extracorporeal blood treatment apparatus and to an extracorporeal blood treatment apparatus comprising a fluid temperature control device (e.g. a warming device) or configured to be coupled to a fluid temperature control device (e.g. a warming device). The present invention relates to a fluid warming or cooling device coupled or configured to be coupled to an extracorporeal blood circuit of the extracorporeal blood treatment apparatus to heat or cool blood (blood warming/cooling device). The present invention relates to a fluid warming/cooling device coupled or configured to be coupled to a treatment fluid circuit of the extracorporeal blood treatment apparatus to heat/cool treatment fluid (treatment fluid warming/cooling device). In particular, the present invention relates to the detection of the presence of a disposable fluid warming/cooling bag in the fluid warming device. Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example. Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment. During extracorporeal blood treatment therapies, the patient may loose significant amount of heat due to fluid exchange by diffusion or convection, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic haemodialysis (HD), and in the case of low volume but continuous therapies like continuous renal replacement therapy (CRRT). Furthermore, the risk of hypothermia is even more problematic in case of treatments applied to low body weight patients, such as children. Blood cooling due to fluid exchange (dialysate, infusion or both) or due to water evaporation during gas exchange processes is usually more important than heat losses to atmosphere in the complete extracorporeal blood circuit.

In order to prevent hypothermia during extracorporeal blood treatment, blood warmers acting on the bloodline and capable of directly warming blood and treatment fluid warmers acting on the treatment fluid circuit to heat treatment fluid/s prior to their infusion in the blood circuit or treatment unit have been used.

BACKGROUND

Document DE 10 2013 221 804 relates to a bag warmer for heating a liquid in a liquid heat bag. The bag warmer is used in dialysis and other continuous therapies. The bag warmer is provided with an electric switch which is used to detect if the liquid heat bag is properly arranged in its predetermined operating position. The electric switch is a pushbutton which can be activated or actuated directly by the liquid heat bag. Document U.S. Pat. No. 6,535,689 relates to an intravenous fluid warming system with a removable heat exchanger which includes a presence detector. The system includes a warming unit for warming the fluid and an inlet slot for receiving a heat exchanger which is embodied as a cassette. A heat exchanger presence detector is part of the warming system. The presence detector detects the presence of the heat exchanger when it is received between as first and a second heater plate of the warming unit. In one embodiment, a portion of the heat exchanger presence detector comprises a magnet located on or in the first heater plate and a sensor located in a slot in the second heater plate. Document U.S. Pat. No. 6,535,689 discloses that the cassette presence may be sensed by other types of switches such as: an optical switch where the cassette interrupts a light beam or where a hole in the cassette allows a light beam through; a mechanical switch that the cassette hits or activates when it is properly inserted into the warming unit; or other types of electrical, magnetic, optical, and/or mechanical switches. Disadvantages of most of the cited prior art presence detectors are related to lack of reliability and bulkiness. Indeed, presence detectors employing mechanical switches with moving parts, like DE 10 2013 221 804, may be subject to mechanical failures and/or locking of the moving parts. Presence detectors employing a transmitter below the bag and a receiver above with a straight path between transmitter and receiver, like the one disclosed in U.S. Pat. No. 6,535,689, may lose alignment and provide a false signal, in particular when the warmer is opened and closed to clean it and/or for maintenance. Indeed, variability was observed between opening and closing of the warmer due to variability in the alignment of the pair (transmitter and receiver). Furthermore, moving parts, like in DE 10 2013 221 804, and presence of elements of the detector on both sides of the slot for receiving the bag, like in U.S. Pat. No. 6,535,689, requires space and may increase the height and/or bulkiness of the warming device.

SUMMARY OF THE INVENTION

In view of the above, it is an object of embodiments according to the present invention to improve the reliability of the fluid warming devices for extracorporeal blood treatment apparatuses using disposable warming bags and to improve the reliability of the extracorporeal blood treatment apparatuses employing said fluid warming devices. In particular, it is an object to provide a fluid warming device wherein the reliability of detecting the presence of the fluid warming bag is improved. It is a further object to improve the reliability of detecting the correct position of the fluid warming bag inside the seat for accommodating said fluid warming bag. It is a further object to provide a presence detector in a fluid warming/cooling device which is reliable, accurate and compact. At least one of the above objects is substantially achieved by exploiting the reflective properties of the fluid warming bag to monitor its presence and/or orientation in the heating seat. In particular, at least one of the above objects is substantially achieved by a fluid temperature control (e.g. warming/cooling) device according to one or more of the appended claims. Aspects of the invention are disclosed in the following. General reference is made to warming fluid; however the disclosed device is intended for temperature control of the fluid, such as warming or cooling the fluid.

In accordance with a $1^{st}$ independent aspect, a fluid temperature control (e.g. warming/cooling) device for an extracorporeal blood treatment apparatus, comprises:
- a casing delimiting a heating seat configured to accommodate a fluid warming bag connected or connectable to an extracorporeal blood treatment apparatus;
- heating elements operatively active in the heating seat to heat the fluid warming bag;
- at least a presence detector operatively active in the heating seat to detect the presence of the fluid warming bag;
- wherein the presence detector comprises a transmitter of a signal and a receiver;
- wherein the receiver is positioned with respect to the transmitter to selectively receive a transmitted signal after reflection;
- optionally wherein the receiver is positioned with respect to the transmitter either:
  - to receive a signal emitted by the transmitter and reflected by the fluid warming bag only when the fluid warming bag is properly accommodated in the heating seat; or
  - to receive a signal emitted by the transmitter and reflected by the fluid warming bag only when the fluid warming bag is not properly accommodated in the heating seat; or
  - to receive a signal emitted by the transmitter after reflection, at least a property (e.g. intensity) of the reflected signal varying based upon the fluid warming bag being properly accommodated in the heating seat or not.

In accordance with a $2^{nd}$ independent aspect, an extracorporeal blood treatment apparatus, comprises:
- a blood treatment device;
- an extracorporeal blood circuit coupled to the blood treatment device;
- a blood pump; a pump section of the extracorporeal blood circuit being configured to be coupled to the blood pump;
- optionally a treatment fluid circuit operatively connected to the extracorporeal blood circuit and/or to the blood treatment device;
- at least a fluid temperature control (e.g. warming/cooling) device coupled or configured to be coupled to the extracorporeal blood circuit to heat blood and/or to the treatment fluid circuit to heat the treatment fluid/s;
- wherein the fluid temperature control (e.g. warming/cooling) device is according to the $1^{st}$ aspect and/or includes one or more of the following aspects.

The transmitter and the receiver are in particular an electromagnetic transmitter and an electromagnetic receiver.

The emitted signal is in particular an electromagnetic radiation which is reflected either by the fluid warming bag (when present and placed in the heating seat) or by a receiving surface of the casing placed opposite the transmitter in case the fluid warming bag is not in the heating seat. The presence of the fluid warming bag in the heating seat alters a property of the reflected signal, such as the reflection path and/or the signal intensity and allows to determine presence or absence of the fluid warming bag.

In a first embodiment, the presence of the fluid warming bag reflects the signal directly from the electromagnetic transmitter towards the electromagnetic receiver. In such a case, only when the fluid warming bag is in correct place in the heating seat, the transmitted signal is reflected by the bag and received by the receiver. If the fluid warming bag is removed from the heating seat, the transmitted signal is reflected by the receiving surface of the casing, deflected to a modified path, and no more received by the receiver. Presence of the fluid warming bag is detected only upon receiving the reflected signal. In an alternative embodiment, in case the fluid warming bag is not in the heating seat, the transmitted signal is reflected by the receiving surface of the casing and received by the receiver. If the fluid warming bag is properly inserted into the heating seat, the transmitted signal is reflected and deflected to a modified path by the bag and no more received by the receiver. Presence of the fluid warming bag is detected upon failure to receive the reflected signal.

In a further embodiment, the emitted signal is reflected and received by the receiver independently of the presence of the fluid warming bag into the heating seat (i.e. the reflected signal is always received by the receiver); however, presence or absence of the fluid warming bag alters one or more of the reflected signal properties (e.g. intensity, phase, wavelength, etc.) and therefore presence or absence of the fluid warming bag can be ascertained by elaborating the received reflected signal. For example, the casing receiving surface may absorb most of the signal (i.e. the reflected signal is highly damped) while the fluid warming bag may have a highly reflective surface (i.e. the reflected signal is high intensity).

In all embodiments, the transmitter and the receiver may remain static relative to each other, independent of movement of other parts of the fluid warming/cooling device, and this feature improves precision and/or reliability of the detection. Notably, the emitter and receiver may be the same device, i.e. the emitter itself, after emitting the signal, receives the reflected signal (e.g. an emitting antenna receives the reflected signal). Alternatively the emitter and receiver may be different and separate devices.

Furthermore, even if the emitter and receiver are different and separate devices, they may be placed substantially in the same position (e.g. vertically placed over the fluid warming bag). In a further independent aspect an assembly of a fluid warming/cooling device (as per the described aspects) and of a fluid warming/cooling bag (as per the described aspects) is provided.

In a $3^{rd}$ aspect according to the $1^{st}$ or $2^{nd}$ aspect, the fluid warming/cooling device is a blood warming/cooling device and is coupled or configured to be coupled to the extracorporeal blood circuit to heat blood.

In a 4th aspect according to the 1st, 2nd or 3rd aspect, the fluid warming/cooling device is a treatment fluid warming/cooling device and is coupled or configured to be coupled the treatment fluid circuit to heat treatment fluid/s.

In a 5th aspect according to any of the previous aspects 1 to 4, the fluid warming/cooling device comprises a receiving surface arranged to intercept the signal emitted by the transmitter optionally when the fluid warming bag is not accommodated or is not properly accommodated in the heating seat.

In a 6th aspect according to the previous aspect, the receiving surface is configured to absorb, at least in part, the signal emitted by the transmitter.

In a 7th aspect according to the previous aspect 5 or 6, the receiving surface is configured to reflect, at least in part, the signal emitted by the transmitter.

In an 8th aspect according to any of the previous aspect 5 to 7, the receiving surface is arranged to reflect the signal along a first reflected path.

In a 9th aspect according to the previous aspect 8, the receiver is spaced from said first reflected path.

In a 10th aspect according to the previous aspect 8 or 9, the signal reflected along the first reflected path is not captured by the receiver.

In a 11th aspect according to any of the previous aspects 5 to 10, the signal received by the receiving surface is in part reflected and in part absorbed and the part reflected is not captured by the receiver.

In a 12th aspect according to the previous aspect, the receiving surface is dark and/or presents a matte finish.

In a 13th aspect according to any of the previous aspects 5 to 12, the casing comprises two, optionally parallel and optionally flat, opposite surfaces delimiting the heating seat.

In a 14th aspect according to previous aspect 13, the receiving surface is a part of one of said opposite surfaces.

In a 15th aspect according to previous aspect 13 or 14, the receiving surface is sloping with respect to the rest of said one of said opposite surfaces.

In a 16th aspect according any of the previous aspects 13 to 15, the transmitter is placed on a side of the heating seat opposite with respect to the receiving surface.

In a 17th aspect according any of the previous aspects 1 to 16, an outer surface of the fluid warming bag is configured to reflect, at least in part, the signal emitted by the transmitter.

In an 18th aspect according the previous aspect 17, the outer surface is arranged to reflect the signal along a second reflected path.

In a 19th aspect according the previous aspect 18, when the fluid warming bag is properly accommodated in the heating seat, the receiver intercepts said second reflected path.

In a 20th aspect according any of the previous aspects 17 to 19 when according to aspects 5 to 16, the receiving surface is sloping with respect to the outer surface of the fluid warming bag when the fluid warming bag is properly accommodated in the heating seat.

In a 21st aspect according to any of the previous aspects 17 to 20, the outer surface of the fluid warming bag presents a gloss finish.

In a 22nd aspect according to any of the previous aspects 5 to 16 or according to any of aspects 17 to 21 when aspect 17 is according to any of aspects 5 to 16, when the fluid warming bag is properly accommodated in the heating seat, said fluid warming bag is positioned between the transmitter and the receiving surface.

In a 23rd aspect according to previous aspect 22, when the fluid warming bag is properly accommodated in the heating seat, said fluid warming bag covers the receiving surface.

In a 24th aspect according to any of the previous aspects 1 to 23, the transmitter and the receiver are positioned on a same side with respect to the heating seat and, when the fluid warming bag is in the heating seat, on a same side with respect to the fluid warming bag.

In a 25th aspect according to any of the previous aspects 17 to 21 or according to any of the previous aspects 22 and 24 when according to any of aspects 17 to 21, when the fluid warming bag is properly accommodated in the heating seat, the transmitter and the receiver are arranged symmetrical with respect to a symmetry axis orthogonal to the outer surface of the fluid warming bag.

In a 26th aspect according to the previous aspect 25, when the fluid warming bag is properly accommodated in the heating seat, each of the transmitter and the receiver is positioned with an angle with respect to the outer surface of the fluid warming bag between 30° and 60°, optionally of 45°.

In a 27th aspect according to the previous aspect 18 or 19 or to previous aspect 24 or 25 when according to aspect 18 or 19, the signal is emitted by the transmitter along an emitted path.

In a 28th aspect according to previous aspect 27, the emitted path and the second reflected path are symmetrically arranged with respect to a symmetry axis orthogonal to the outer surface of the fluid warming bag.

In a 29th aspect according to previous aspect 28, the emitted path and the second reflected path delimit between them an angle between 60° and 120°, optionally of 90°.

In a 30th aspect according to any of previous aspects 1 to 29, the fluid warming bag is substantially flat.

In a 31st aspect according to any of previous aspects 1 to 30, the fluid warming bag comprises a main portion delimiting a fluid path with an inlet and an outlet.

In a 32nd aspect according to the previous aspect 31, the fluid warming bag comprises a tab protruding from the main portion.

In a 33rd aspect according to the previous aspect 32, the tab confers an asymmetric shape to the fluid warming bag.

In a 34th aspect according to the previous aspect 32 or 33, the heating seat presents a main seat and a recess for accommodating the tab only when the fluid warming bag is properly accommodated in the heating seat; wherein, optionally, the recess is positioned on a side of the main seat. The heating seat follows the shape of the fluid warming bag, which will not allow for complete insertion of the fluid warmer bag if it is inserted in wrong/reverse orientation.

In a 35th aspect according the any of the previous aspects 32 to 34, the signal is reflected by the tab.

In a 36th aspect according to any of the previous aspects 32 to 35 when aspect 31 is according to any of aspects 17 to 21, the tab carries the outer surface of the fluid warming bag.

In a 37th aspect according to any of the previous aspects 32 to 36 when aspect 31 is according to any of aspects 22 or 23, the tab is positioned between the transmitter and the receiving surface or covers the receiving surface.

In a 38th aspect according to aspect 34 when aspect 31 is according to any of aspects 5 to 16, the recess comprises the receiving surface.

In a 39th aspect according to any of previous aspects 1 to 38, the fluid warming/cooling device comprises two presence detectors configured to detect the presence of at least two different types of fluid warming bag, optionally of three different types of fluid warming bag.

In a 40th aspect according to any of previous aspects 1 to 39, the fluid warming/cooling device comprises a first presence detector and a second presence detector.

In a 41st aspect according to previous aspect 40, the first presence detector is arranged to emit the signal onto an outer surface of the fluid warming bag of a first type or of a second type only when the fluid warming bag of the first type or of the second type is properly accommodated in the heating seat.

In a 42nd aspect according to any of the previous aspects 40 or 41, the second presence detector is arranged to emit the signal onto an outer surface of the fluid warming bag of the first type or of a third type only when the fluid warming bag of the first type or of the third type is properly accommodated in the heating seat.

In a 43rd aspect according to any of the previous aspects from 40 to 42, the first presence detector and the second presence detector are placed side by side.

In a 44th aspect according to any of the previous aspects from 41 to 43 when aspect 40 is according to according to any of aspects 32 to 38, the tabs of the fluid warming bags of the first, second and third type are different in shape and/or position with respect to the respective main portion.

In a 45th aspect according to any of previous aspects 1 to 44, the casing comprises an upper part and a lower part, wherein the heating seat is delimited between said upper part and said lower part.

In a 46th aspect according to the previous aspect 45, the upper part and the lower part can be, at least in part, spaced from one another to open the heating seat, in particular the upper part and the lower part may be hinged one another.

In a 47th aspect according to the previous aspect 45 or 46, said at least a presence detector is mounted on the upper part.

In a 48th aspect according to previous aspect 45 or 46 or 47 when aspect 45 is according to any of aspects 5 to 16, the receiving surface is positioned on the lower part.

In a 49th aspect according to any of previous aspects 1 to 48, the transmitter and the receiver are optoelectronic devices.

In a 50th aspect according to any of previous aspects 1 to 49, the signal is light.

In a 51st aspect according to any of previous aspects 1 to 50, the transmitter is a light emitting diode (LED) and the receiver is a photodiode. The presence of the reflected light on the photodiode indices a voltage on an anode of the photodiode allowing the detection of the bag.

In a 52nd aspect according to the previous aspect 51, a wavelength of the emitted light is between 465 nm and 475 nm, optionally of 470 nm.

In a 53rd aspect according to any of the previous aspects 1 to 52, the fluid warming/cooling device and/or the extracorporeal blood treatment apparatus comprises an electronic control unit operatively connected to said at least a presence detector.

In a 54th aspect according to previous aspect 53, the electronic control unit is configured to perform at least the following procedure:
  receiving signals from the presence detector (in particular the receiver receiving the reflected signal),
  analyzing the received signals,
  detecting if the fluid warming bag and/or which type of fluid warming bag is properly accommodated in the heating seat as a function of the analyzed received signals.

In a 55th aspect according to previous aspect 54, the electronic control unit is configured to provide an alarm and/or to stop and/or to prevent operation of the fluid warming/cooling device if the fluid warming bag is not properly accommodated in the heating seat.

In a 56th aspect according to previous aspect 54 or 55, the electronic control unit is configured to provide a signal indicating if the fluid warming bag and/or which type of fluid warming bag is properly accommodated in the heating seat.

DESCRIPTION OF DRAWINGS

The following drawings relating to aspects of the invention are provided by way of non-limiting example.

DETAILED DESCRIPTION

Figure 1:
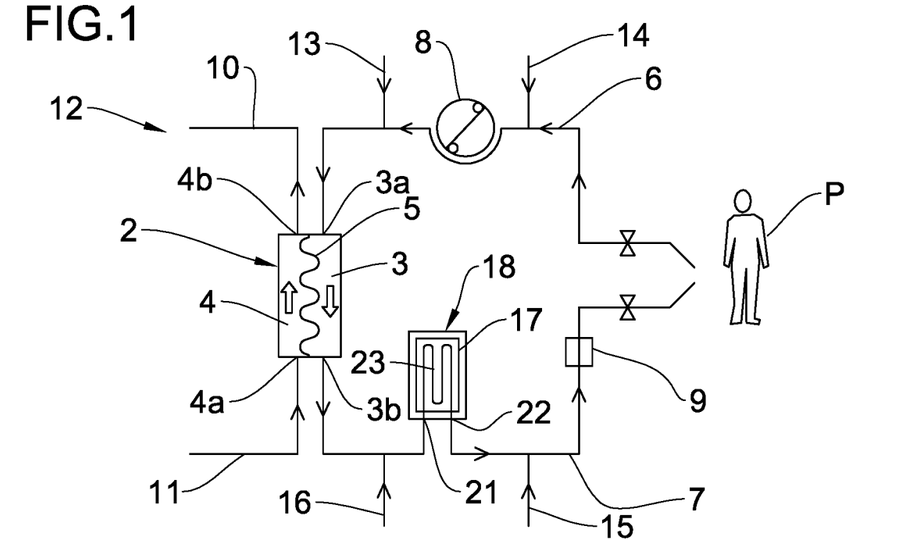
FIG. 1 shows a schematic representation of an extracorporeal blood treatment apparatus provided with a fluid warming/cooling device according to the present invention.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter, an absorber or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6.

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device 9 operating on the blood return line 7 (the air trapping device 9 may be a venous deaeration chamber). The air trapping device 9 is placed online in the blood return line 7.

A first section of the blood return line 7 puts in fluid communication the outlet port 3b of the blood chamber 3 with the air trapping device 9 and a second section of the blood return line 7 puts in fluid communication the air trapping device 9 with the patient P. The blood coming from the blood chamber 3 of the treatment device 2 enters and exits the air trapping device 9 before reaching the patient P.

The apparatus 1 of FIG. 1 further comprises one fluid evacuation line 10 connected with an outlet port 4b of the fluid chamber 4 such as to receive the filtered waste fluid through the semipermeable membrane 5. The fluid evacuation line 10 receives such filtered waste fluid coming from the fluid chamber 4 of the treatment device 2, for example, comprising used dialysis liquid and/or liquid ultra-filtered through the membrane 5. The fluid evacuation line 10 leads to a receiving element, not shown, for example having a collection bag or a drainage pipe for the waste fluid. One or more dialysate pumps, not shown, may operate on the fluid evacuation line 10.

In the example of FIG. 1, a dialysis line 11 is also present for supplying a fresh treatment fluid into the inlet port 4a of the fluid chamber 4. The presence of this dialysis line 11 is not strictly necessary since, in the absence of the dialysis line 11, the apparatus 1 is still able to perform treatments such as ultrafiltration, hemofiltration or plasma-filtration. In case the dialysis line 11 is present, a fluid flow intercept device may be used, not shown, to selectively allow or inhibit fluid passage through the dialysis line 11, depending on whether or not a purification by diffusive effect is to be performed inside the treatment device 2.

The dialysis line 11, if present, is typically equipped with a dialysis pump and is able to receive a fresh fluid from a module, not shown, for example a bag or on-line preparation section of dialysis fluid, and to send such a fluid to the inlet port 4a of the fluid chamber 4. The fluid evacuation line 10, the dialysis line 11 and the fluid chamber 4 are part of a treatment fluid circuit 12.

The apparatus 1 as shown in FIG. 1 further comprises an infusion circuit comprising one or more infusion lines of a replacement fluid. According to the embodiment of FIG. 1, a pre-infusion line 13 is connected to the blood withdrawal line 6 between the blood pump 8 and the inlet port 3a of the blood chamber 3. A pre pump infusion line 14 is connected to the blood withdrawal line 6 upstream of the blood pump 8, between said blood pump 8 and the vascular access device inserted in the fistula on the patient P.

A post-infusion line 15; 16 is connected to the blood return line 7 for performing HF or HDF treatments. Generally one or two post-infusion lines are used connected upstream of or to the air trapping device 9. FIG. 1 shows that the post-infusion line comprises a first and a second branch 15, 16. Each of the pre- and/or post-infusion line 13, 14, 15, 16 is provided with a respective pump, not shown. The pre- and/or post-infusion lines 13, 14, 15, 16 may be supplied by fluid coming from bags or directly by infusion fluid prepared on-line. Each of the pre- and/or post-infusion lines 13, 14, 15, 16 are part of the treatment fluid circuit 12. The specific configuration of the pre- and post-infusion circuits may of course differ from those shown in FIG. 1.

The blood return line 7 presents a heated/cooled portion, for example interposed between the first and second branches 15, 16 of the post-infusion line. In said heated/cooled portion blood is warmed/cooled before flowing into the blood circulation system of the patient P.

The heated/cooled portion is part of a disposable blood warming/cooling bag 17 which is inserted into a blood temperature controlling (e.g. warming/cooling) device 18. The blood warming/cooling device 18 is connected to or is part of the extracorporeal blood treatment apparatus 1. In the following reference is made to a warming device and a warming bag to heat blood. However, the described embodiments are intended in general to cover a device for temperature control of the fluid (e.g. blood), such as warming or cooling.

Figures 2, 3:
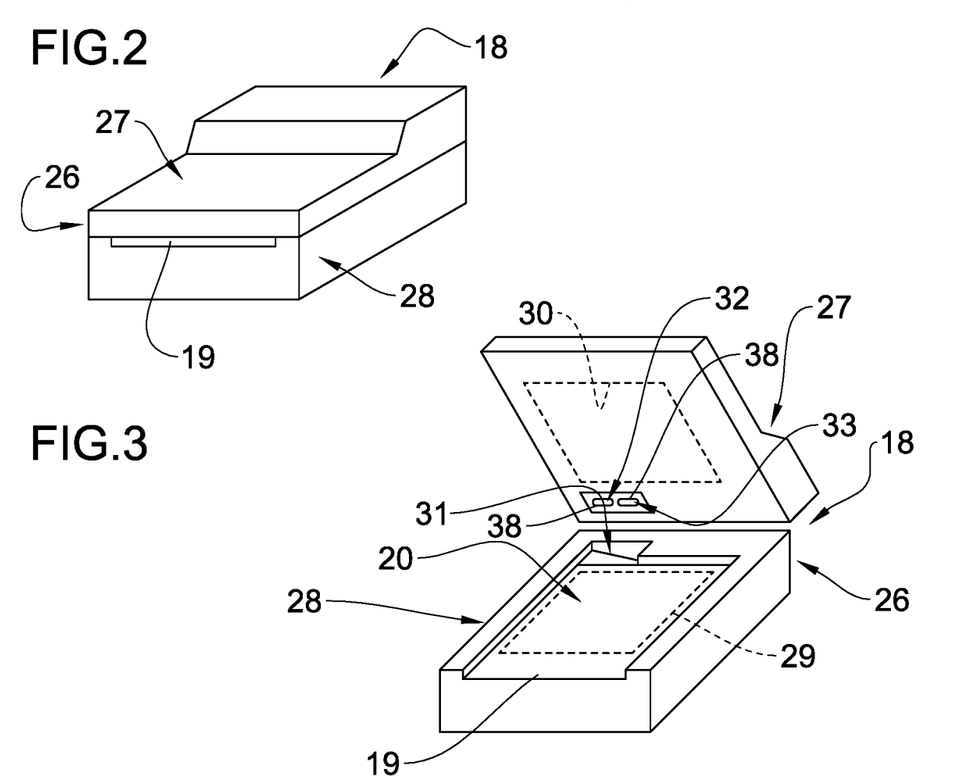
FIG. 2 shows a schematic perspective view of the fluid warming/cooling device of FIG. 1.
FIG. 3 shows the fluid warming/cooling device of FIG. 1 in an open configuration.

The blood warming bag 17 shown in the attached figures is a substantially flat and soft bag insertable through a slot 19 in a heating seat 20 provided in the blood warming device 18 (FIGS. 2 and 3). A thickness of the blood warming bag 17 may 1.5 mm to 3 mm. In a plan view the bag 17 is substantially rectangular with a length of approx 200 mm and a width of approx 100 mm.

The blood warming bag 17 presents an inlet 21 and an outlet 22 connected to the extracorporeal blood circuit. For instance, the blood warming bag 17 comprises two sheets of plastic (e.g. polyurethane or polyvinylchloride) superposed and welded to form the bag and to form, inside the bag, a blood path 23 delimited by said two sheets and by lines of welding.

Figure 4:
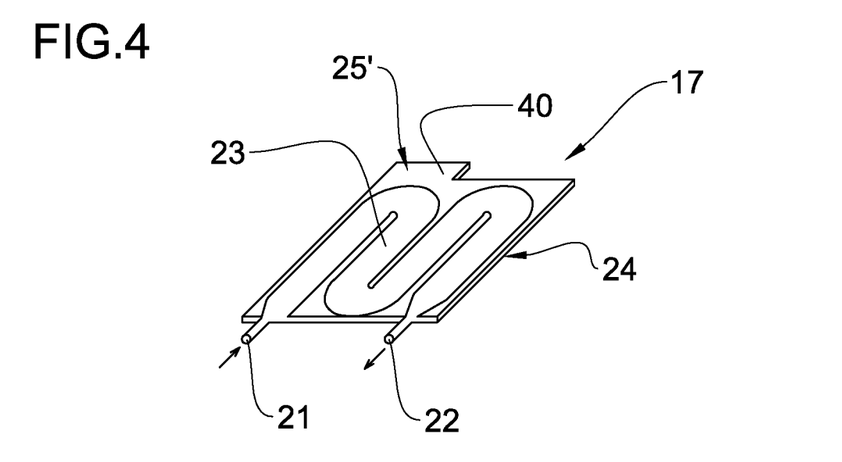
FIG. 4 is a disposable fluid warming bag to be used with the fluid warming/cooling device of FIGS. 2 and 3.

As shown in FIG. 4, the blood warming bag 17 comprises a main portion 24, delimiting the blood path 23 with the inlet 21 and the outlet 22, and a tab 25', 25", 25''' protruding from the main portion 23 on a side of the main portion 24 opposite to the inlet 21 and the outlet 22. Looking at the blood warming bag 17 in plan view, the tab 25', 25", 25''' is positioned aside with respect to an axis interposed between the inlet 22 and the outlet 22 such that the blood warming bag 17 has an asymmetric shape.

Figure 5A:
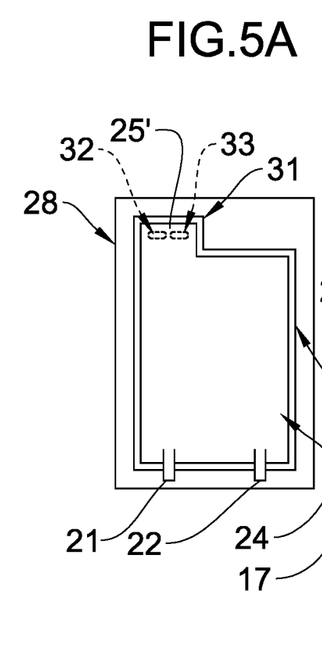
FIGS. 5A to 5C show top views of a lower part of the fluid warming/cooling device of FIGS. 2 and 3 with different types of fluid warming bag.
Figure 5B:
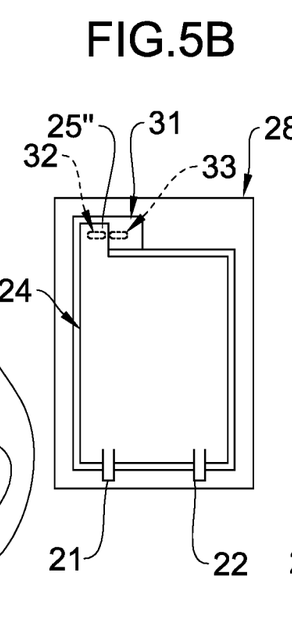
Figure 5C:
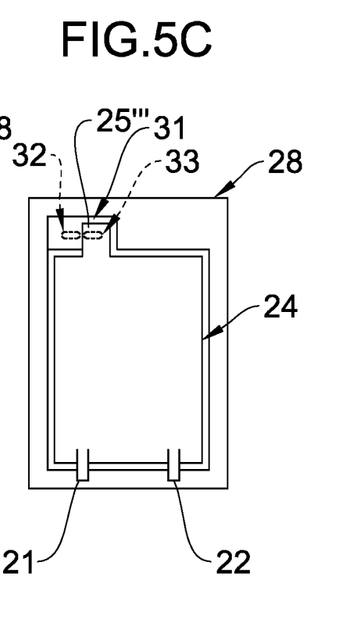
Figure 6:
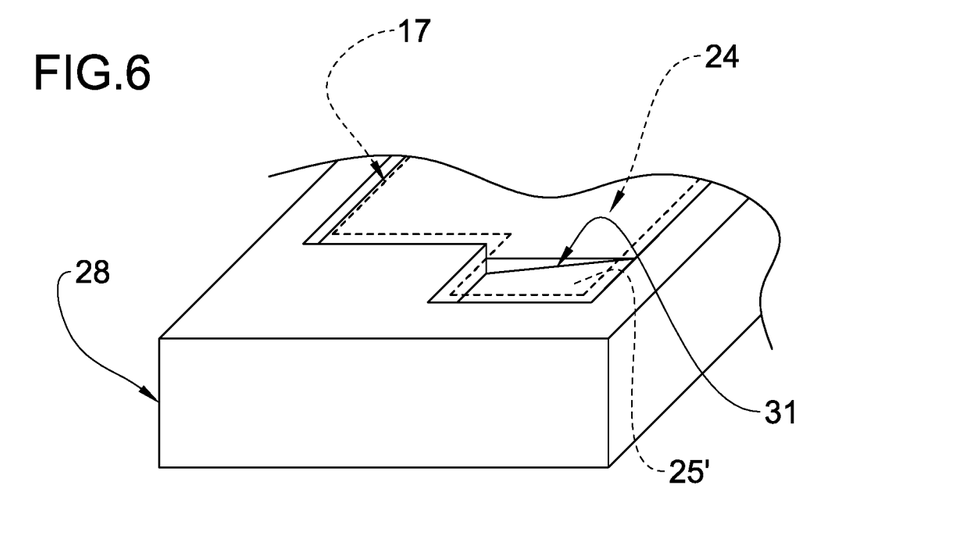
FIG. 6 shows an enlarged view of a portion of the lower part of the fluid warming/cooling device of FIGS. 2 and 3.

FIGS. 5A, 5B and 5C show three different types of blood warming bag 17. The plan view of the main portion 24 of the three different types is the same. The three types may differ for other features, such as the volume of liquid contained in the main portion 24 and/or the shape/dimensions of the blood path 23 and/or the thickness of the bag.

A first type of blood warming bag 17, shown in FIG. 5A, has a first type of tab 25' positioned to the left with respect to the main portion 24. A second type of blood warming bag 17, shown in FIG. 5B, has a second type of tab 25" which is positioned to the left with respect to the main portion 24 and has a smaller width than the first type of tab 25. A third type of blood warming bag 17, shown in FIG. 5C, has a third type of tab 25''' which is shifted to the right with respect the second type of tab 25" and has the same width as said second type of tab 25".

The blood warming device 18 comprises a casing 26 delimiting the heating seat 20 configured to accommodate the blood warming bag 17. The casing 26 comprises an upper part 27 and a lower part 28 which are linked and movable between a working configuration (shown in FIG. 2) and a maintenance configuration (shown in FIG. 3). The upper part 27 and lower part 28 of FIGS. 2 and 3 are hinged to move between the mentioned configurations.

When the casing 26 is in the working configuration of FIG. 2, the upper part 28 and the lower part 28 are juxtaposed and delimit inside the casing 26 the heating seat 20 which opens outside through the slot 19. The heating seat 20 and the slot 19 have a height slightly greater than the thickness of the blood warming bag to allow insertion of the bag through the slot 19 when the bag is deflated. The height of the heating seat 20 and of the slot 19 may be 1.3 mm to 3.2 mm.

When the casing 26 is in the maintenance configuration of FIG. 3, the upper part 27 is rotated and raised with respect to the lower part 28 to open the heating seat 20 and to allow maintenance operations and/or cleaning.

An upper face of the lower part 28 has a hollow delimiting a lower part of the heating seat and shaped to accommodate the blood warming bag 17. The hollow presents a first flat surface or plate heated by a first heating element 29 placed underneath said first surface or plate. A lower face of the upper part 28 has a second flat surface or plate heated by a second heating element 30 placed underneath said second surface or plate. The second flat surface or plate delimits an upper part of the heating seat 20. The first flat surface and the second flat surface are opposite and parallel surfaces delimiting the heating seat 20. The first and second heating elements 29, 30 may be or may be connected to electrical resistors powered by a power source and controlled by an electronic control unit, not shown, in order to heat the blood warming bag.

The heating seat 20 presents a main seat configured to accommodate the main portion 24 of the blood warmer bag 17 and a recess 31 for accommodating the tab 25', 25", 25'''. The first and second flat surfaces delimit the main portion 24.

As shown in FIGS. 3, 5A-5C and 6, the recess 31 is fashioned in the lower portion 28 and it is positioned on a side of the main seat 20 opposite to the slot 19.

The fluid warming device 18 comprises a first presence detector 32 and a second presence detector 33 which are operatively active in the heating seat 20 to detect the presence and the type of the blood warming bag 17. The first presence detector 32 and the second presence detector 33 are mounted on the upper part 27 of the casing 26, are placed side by side and, when the casing 26 is in the working configuration of FIG. 2, said first presence detector 32 and second presence detector 33 face towards the recess 31.

The first presence detector 32 and second presence detector 33 are of the same kind. Therefore, only the structure of the first presence detector 32 will be herewith described. The first presence detector 32 comprises an electromagnetic transmitter 34 and an electromagnetic receiver 35 and a supporting circuitry, not shown. The electromagnetic transmitter 34 is a light emitting diode (LED) and the electromagnetic receiver 35 is a photodiode. The light emitting diode emits a light with a wavelength of 470 nm. The light emitting diode (LED) and the photodiode are of the same type. The electromagnetic transmitter 34 and an electromagnetic receiver 35 are connected to the electronic control unit.

Figure 7:
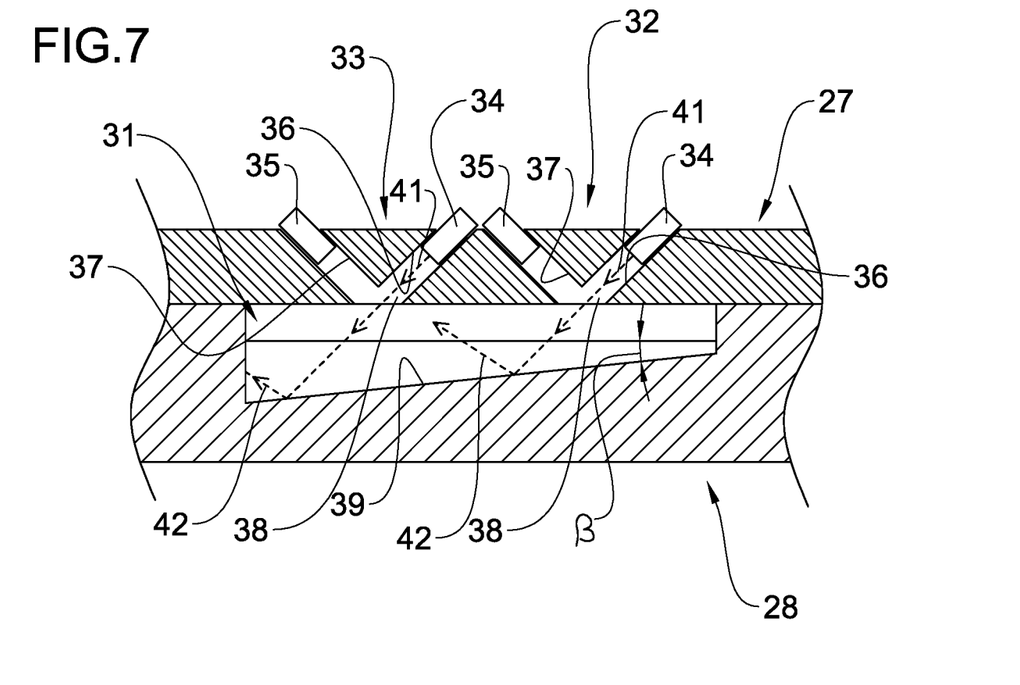
FIG. 7 is a sectioned and enlarged view of a portion of the fluid warming/cooling device of FIGS. 2 and 3.

As shown in FIG. 7, the electromagnetic transmitter 34 is housed in a first passage 36 made in the upper part 27 of the casing 26 and the electromagnetic receiver 35 is housed in a second passage 37 made in the upper part 27 of the casing 26. These first and second passages 36, 37 converges and merges into an opening 38 placed on the lower face of the upper part 27. Said opening 38, when the upper part 26 is juxtaposed to the lower part 28, faces towards the recess 31 in the lower part 28. An angle between these first and second passages 36, 37 is of 90° and each passage delimits with the lower face of the upper part 27 an angle of 45°. The electromagnetic transmitter 34 and the electromagnetic receiver 35 are arranged symmetrical with respect to a symmetry axis orthogonal to the lower face of the upper part 27.

The recess 31 comprises a receiving surface 39 positioned on the bottom of said recess 31. Said receiving surface 39 is spaced from the opening 38 and faces said opening 38 as shown in FIG. 7. A distance between the opening 38 and the receiving surface 39 is greater than the thickness of the heating seat 20.

When the blood warming bag 17 is properly housed in the heating seat 20 and the tab 25', 25", 25''' is in the recess 31, said tab 25', 25", 25''' is above the receiving surface 39 and spaced from the receiving surface 39, as shown in FIG. 7. The tab 25', 25", 25''' is positioned between the first presence detector 32 and the receiving surface 39. With respect to the first presence detector 32, the tab 25', 25", 25''' covers the receiving surface 39 and an upper surface of said tab 25', 25", 25''' closes the opening 38. The receiving surface 39 is sloping with respect to the first flat surface of the main seat 24 and with respect to the lower face of the upper part 27. An angle "β" between the first flat surface and the receiving surface 39 may be 10°. When the blood warming bag 17 is properly accommodated in the heating seat 20 with the tab 25', 25", 25''' in the recess 31, said angle "β" is also between the receiving surface 39 and the tab 25', 25", 25''' (FIG. 7).

The receiving surface 39 is dark and/or presents a matte finish.

An outer surface 40 of the blood warming bag 17 is configured to reflect, at least in part, an electromagnetic radiation emitted by the electromagnetic transmitter 34 only when the blood warming bag 17 is properly accommodated in the heating seat 20.

In the embodiment shown in the attached figures, the outer surface 40 is part of the tab 25', 25", 25'''. The outer surface of the tab 25', 25", 25''' presents a gloss finish. When the blood warming bag 17 is properly accommodated in the heating seat 20 with the tab 25', 25", 25''' in the recess 31, the outer surface 40 is the upper surface of the tab 25', 25", 25'''. The electromagnetic receiver 35 is positioned with respect to the electromagnetic transmitter 34 to receive the electromagnetic radiation emitted by the electromagnetic transmitter 34 and at least in part reflected by the tab 25', 25", 25''' of the blood warming bag 17. Indeed, when the blood warming bag 17 is properly accommodated in the heating seat 20, the electromagnetic transmitter 34 and the electromagnetic receiver 35 are arranged symmetrical with respect to a symmetry axis orthogonal to the upper surface of the tab 25', 25", 25'''.

When the blood warming bag 17 is not properly accommodated in the heating seat 20 and the tab 25', 25", 25''' is not in the recess 31, the receiving surface 39 intercepts the electromagnetic radiation emitted by the electromagnetic transmitter 34. Part of the electromagnetic radiation emitted by the electromagnetic transmitter 34 and received by the receiving surface 39 is in part reflected and in part absorbed and the part reflected is not captured by the electromagnetic receiver 35.

The electromagnetic transmitter 34 emits the electromagnetic radiation along an emitted path 41.

In other words, when the tab 25', 25", 25'" is not in the recess 31, the sloping receiving surface 39 reflects the electromagnetic radiation along a first reflected path 42. The electromagnetic radiation reflected along the first reflected path 42 is not captured by the electromagnetic receiver 34, because the electromagnetic receiver 35 is spaced from said first reflected path 41.

When the tab 25', 25", 25'" is in the recess 31, the outer surface 40 of the tab 25', 25", 25'" reflects the electromagnetic radiation along a second reflected path 43 and the electromagnetic receiver intercepts said second reflected path 43. The emitted path 41 and the second reflected path 43 are symmetrical with respect to a symmetry axis orthogonal to the outer surface 40 of the tab 25', 25", 25'" and delimit between them an angle of 90°.

FIG. 7 shows the emitted path 41 and the first reflected path 42 of both the first presence detector 32 and second presence detector 33 when no tab 25', 25", 25'" is housed in the recess 31 because no blood warming bag 17 is in the heating seat 20 or because the blood warming bag 17 is not fully inserted in said heating seat 20. The first reflected path 42 of both the first presence detector 32 does not reach the respective electromagnetic receiver 35.

Figure 7A:
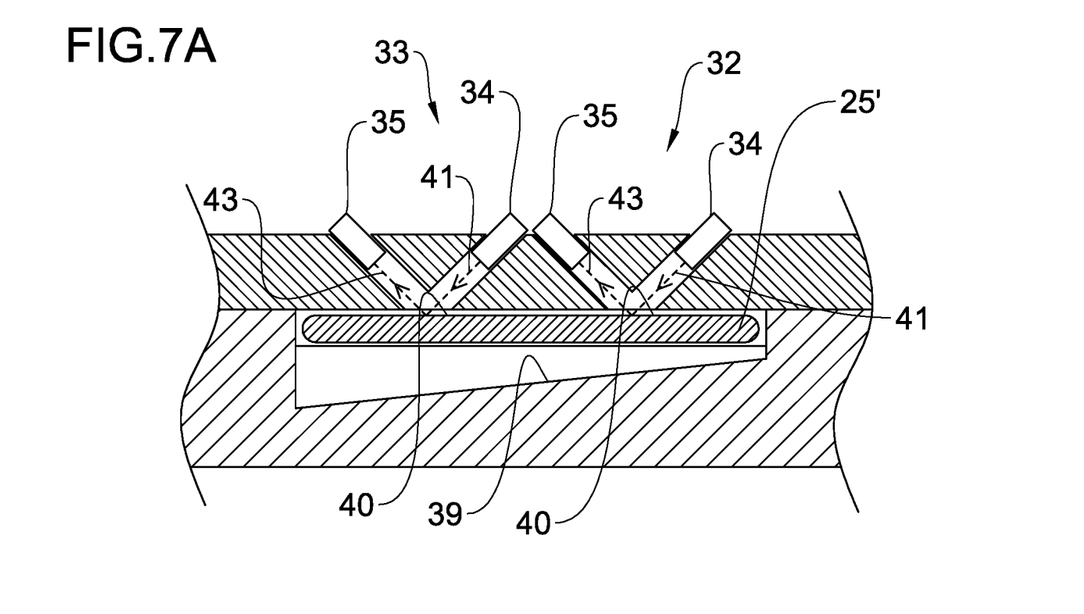
FIGS. 7A to 7C show the portion of FIG. 7 with the different types of fluid warming bag of FIGS. 5A to 5C.

FIG. 7A shows the emitted path 41 and the second reflected path 43 of both the first presence detector 32 and second presence detector 33 when the first type of tab 25' of the first type of blood warming bag 17 is housed in the recess 31, as in FIG. 5A. The second reflected path 43 of both the first presence detector 32 reaches the respective electromagnetic receiver 35. The blood warming bag 17 of the first type is properly accommodated in the heating seat 20.

Figure 7B:
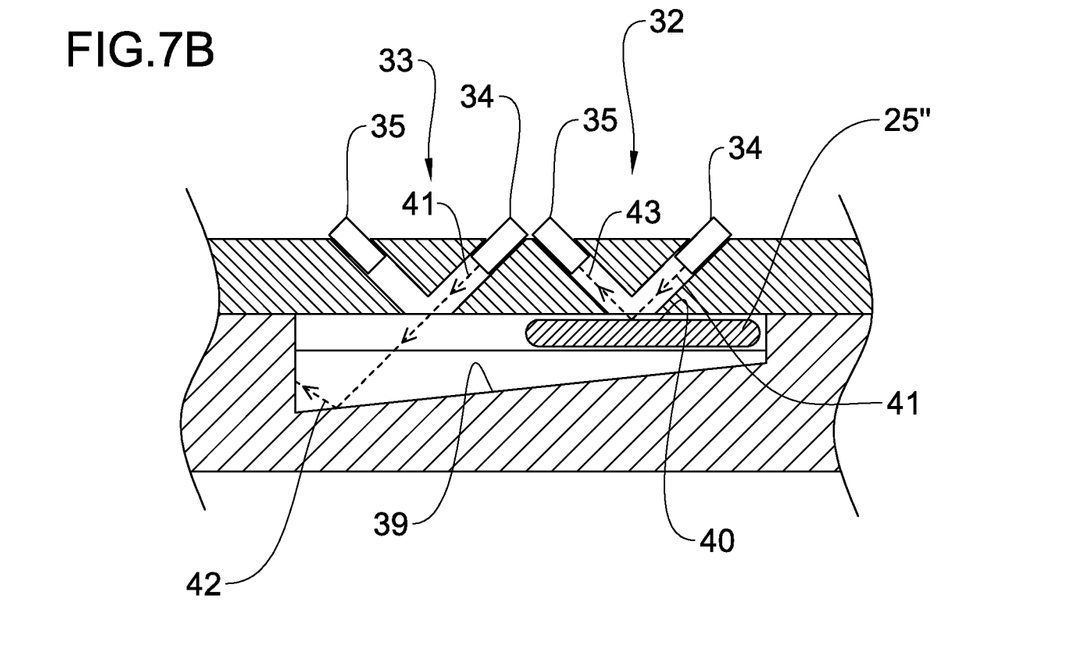

FIG. 7B shows the emitted path 41 and the second reflected path 43 of the first presence detector 32 and the emitted path 41 and the first reflected path 42 of the second presence detector 33 when the second type of tab 25" of the second type of blood warming bag 17 is housed in the recess 31, as in FIG. 5B. The second reflected path 43 of the first presence detector 32 reaches the respective electromagnetic receiver 35. The first reflected path 42 of the second presence detector 33 does not reach the respective electromagnetic receiver 35. The blood warming bag 17 of the second type is properly accommodated in the heating seat 20.

Figure 7C:
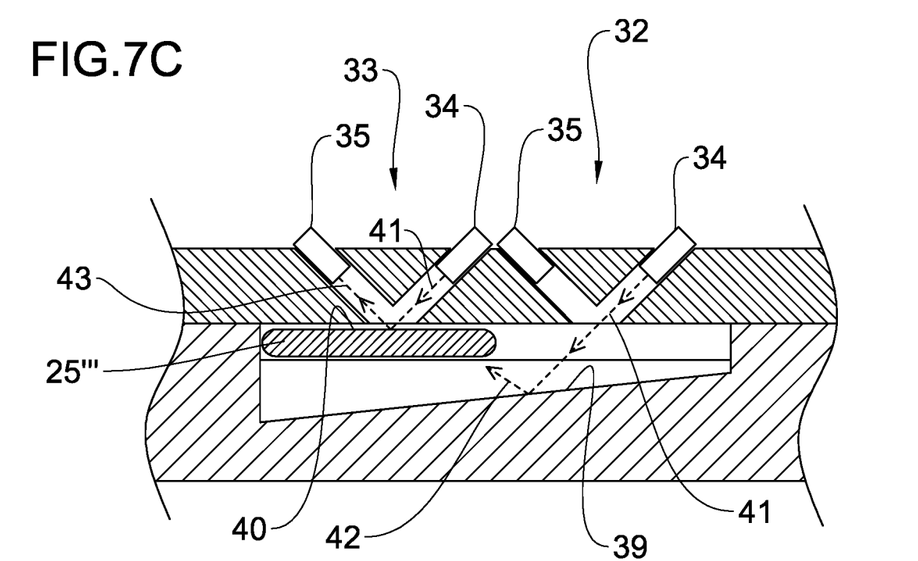

FIG. 7C shows the emitted path 41 and the second reflected path 43 of the second presence detector 33 and the emitted path 41 and the first reflected path 42 of the first presence detector 32 when the third type of tab 25'" of the third type of blood warming bag 17 is housed in the recess 31, as in FIG. 5C. The first reflected path 42 of the first presence detector 32 does not reach the respective electromagnetic receiver 35. The second reflected path 43 of the second presence detector 33 reaches the respective electromagnetic receiver 35. The blood warming bag 17 of the third type is properly accommodated in the heating seat 20.

The electronic control unit receives signals from electromagnetic receivers 35 of the first presence detector 32 and of the second presence detector 33 and analyzes readings to detect if and which type of blood warming bag 17 has been inserted into the blood warming device 18, according to the following table 1.

TABLE 1

| First presence detector | Second presence detector | Bag detection |
|---|---|---|
| False | False | NO BLOOD WARMING BAG |
| True | True | TYPE 1 BAG INSERTED |
| True | False | TYPE 2 BAG INSERTED |
| False | True | TYPE 3 BAG INSERTED |

The electronic control unit may be further configured to provide an alarm and/or to stop and/or to prevent operation of the blood warming device 18 if the blood warming bag 17 is not properly accommodated in the heating seat 20.

Figure 8A:
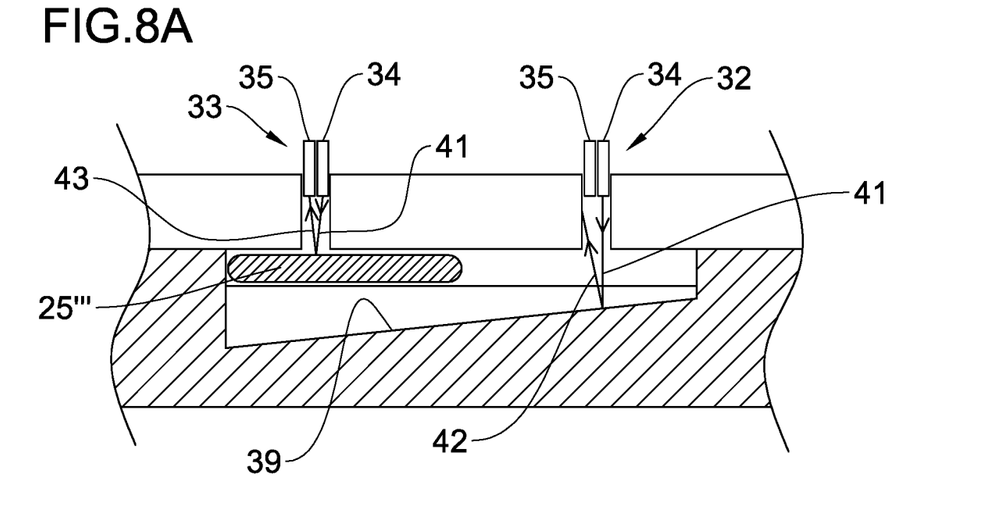
FIGS. 8A and 8B show a sectioned and enlarged view of a portion of the fluid warming/cooling device including additional embodiments of the presence detectors.
Figure 8B:
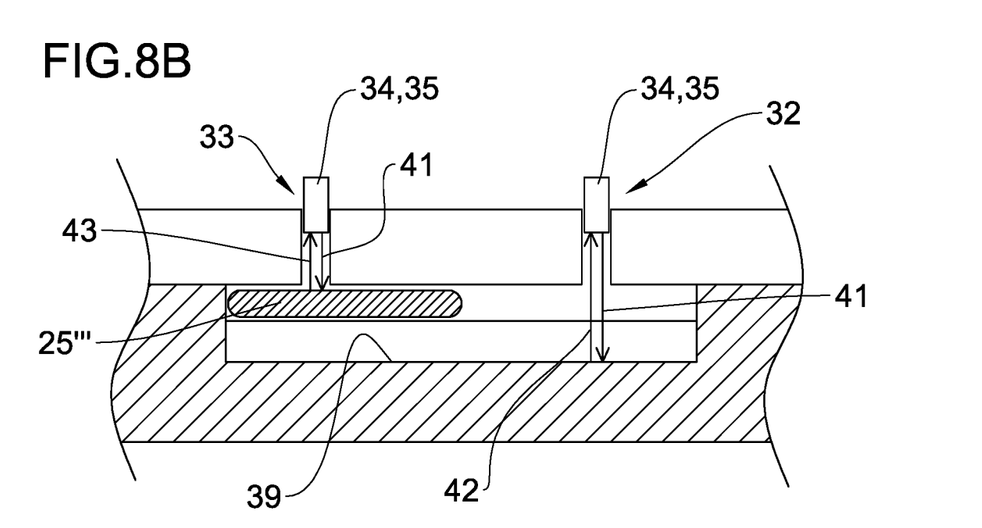

Additional embodiments of the presence detectors are shown in FIGS. 8A and 8B. The embodiment of FIG. 8A shows that the emitter 34 and the receiver 35 of each of the first presence detector 32 and the second presence detector 33 are placed substantially in the same position (e.g. vertically placed over the fluid warming bag 17). The emitter 34 and the receiver 35 of each presence detector 32, 33 are housed in a common passage and vertically oriented with respect to the first flat surface of the main seat 24.

FIG. 8A shows the third type of tab 25'" of the third type of blood warming bag 17 housed in the recess 31, as in FIG. 5C. The first reflected path 42 of the first presence detector 32 is reflected by the receiving surface 39 and does not reach the respective electromagnetic receiver 35. The second reflected path 43 of the second presence detector 33 is reflected by the outer surface 40 of the third type of tab 25'" of the blood warming bag 17 and reaches the respective electromagnetic receiver 35.

The emitter 34 may be only slightly inclined or may be provided with deflecting elements, not shown, so that the emitted signal delimits anyway an angle different form 90° with the outer surface 40 of the blood warming bag 17. Otherwise, even if the emitted signal is substantially perpendicular to the surface 40 of the third type of tab 25'", the receiver 35 is so close to the emitter 34 that the signal by the fluid warming bag 17 is captured by the receiver 35.

The embodiment of FIG. 8B shows that the emitter 34 and the receiver 35 of each of the first presence detector 32 and the second presence detector 33 are the same device. The emitter itself, after emitting the signal, receives the reflected signal (e.g. an emitting antenna receives the reflected signal). Each emitter/receiver 34, 35 is housed in a passage vertically oriented with respect to the first flat surface of the main seat 24. In other embodiments, not shown in the attached figures, the emitted signal is reflected and received by the receiver 35 independently of the presence of the fluid warming bag 17 into the heating seat 31 (i.e. the reflected signal is always received by the receiver). However, presence or absence of the fluid warming bag 17 alters one or more of the reflected signal properties (e.g. intensity, phase, wavelength, etc.) and therefore presence or absence of the fluid warming bag 17 can be ascertained by elaborating the received reflected signal. For example, the casing receiving surface may absorb most of the signal (i.e. the reflected signal is highly damped) while the fluid warming bag 17 may have a highly reflective surface (i.e. the reflected signal is high intensity).

The fluid warming device 1 according to the invention herewith disclosed may be designed to be coupled or configured to be coupled the treatment fluid circuit to heat treatment fluid/s. One or more treatment fluid warming device 1 may be coupled to one or more of the pre- and/or post-infusion lines 13, 14, 15, 16 or the dialysis line 11.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:

1. Fluid temperature control device for an extracorporeal blood treatment apparatus, the fluid temperature control device comprising:
 a casing delimiting a heating/cooling seat configured to accommodate a fluid warming/cooling bag connected or connectable to an extracorporeal blood treatment apparatus;
 heating/cooling element operatively active in the heating/cooling seat to heat/cool the fluid warming/cooling bag;
 a first presence detector operatively active at the heating/cooling seat and configured to detect the presence and type of the fluid warming/cooling bag;
 wherein the first presence detector comprises a first transmitter configured to emit a first signal and a first receiver configured to receive the first signal;
 wherein the first receiver is positioned with respect to the first transmitter to selectively receive first signal from the first transmitter after reflection of the first signal;
 a second presence detector operatively active at the heating/cooling seat and configured w detect the presence and type of the fluid warming/cooling bag;
 wherein the second presence detector comprises a second transmitter configured to emit a second signal and a second receiver configured to receive the second signal;
 wherein the second receiver is positioned with respect to the second transmitter to selectively receive the second signal from the second transmitter after reflection of the second signal; and
 an electronic control unit operatively connected to the first and second presence detectors, the electronic control unit configured to:
  receive a first detector signal from the first presence detector and a second detector signal from the second presence detector,
  analyze the received tint detector signal and the received second detector signal,
  determine, based on the received and analyzed first and second detector signals, when the fluid warming/cooling bats is properly accommodated in the heating/cooling seat and a type of the fluid warming/cooling bag accommodated in the heating/cooling seat.

2. The fluid temperature control device of claim 1, wherein the first receiver is positioned with respect to the first transmitter either:
 to receive the first signal emitted by the first transmitter and reflected by the fluid warming/cooling bag only when the fluid warming/cooling bag is properly accommodated in the heating/cooling seat; or
 to receive the first signal emitted by the first transmitter and reflected by the fluid warming/cooling bag only when the fluid warming/cooling bag is not properly accommodated in the heating/cooling seat.

3. The fluid temperature control device of claim 1, wherein the first receiver is positioned with respect to the first transmitter to receive the first signal emitted by the first transmitter after reflection, wherein at least one property of the first signal varies after reflection of the first signal based upon the fluid warming/cooling bag being properly or not properly accommodated in the heating/cooling seat.

4. The fluid temperature control device of claim 1, comprising a receiving surface configured to intercept the first signal emitted by the first transmitter when the fluid warming/cooling bag is either properly accommodated or not properly accommodated in the heating/cooling seat, wherein the receiving surface is configured to absorb at least a portion of the first signal emitted by the first transmitter.

5. The fluid temperature control device of claim 4, wherein the receiving surface is configured to reflect the first signal along a first reflected path, wherein the first receiver is spaced from said first reflected path such that the first signal reflected along the first reflected path is not captured by the first receiver.

6. The fluid temperature control device of claim 4, wherein the receiving surface comprises a dark and/or matte finish configured to absorb at least a portion of the first signal emitted by the first transmitter.

7. The fluid temperature control device of claim 4, wherein the casing comprises two opposite surfaces delimiting the heating/cooling seat, wherein a receiving surface is a part of one of said two opposite surfaces, and wherein the receiving surface is sloping with respect to the rest of said one of said two opposite surfaces.

8. The fluid temperature control device of claim 4, wherein the first signal received by the receiving surface is in part reflected and in part absorbed and the part reflected is not captured by the first receiver.

9. The fluid temperature control device of claim 4, wherein, when the fluid warming/cooling bag is properly accommodated in the heating/cooling seat, said fluid warming/cooling bag is positioned between the first transmitter and the receiving surface.

10. The fluid temperature control device of claim 9, wherein, when the fluid warming/cooling bag is properly accommodated in the heating/cooling seat, said fluid warming/cooling bag covers the receiving surface.

11. The fluid temperature control device of claim 4, wherein the casing comprises an upper part and a lower part and the heating/cooling seat is delimited between said upper part and said lower part, wherein the first presence detector is mounted on the upper part and the receiving surface is positioned on the lower part, the upper part and the lower part being, at least in part, spaced from one another to open the heating/cooling seat.

12. The fluid temperature control device of claim 1, wherein the casing comprises two opposite surfaces delimiting the heating/cooling seat, wherein the receiving surface is a part of one of said opposite surfaces and is sloping with respect to the rest of said one of said opposite surfaces, wherein the first transmitter is placed on a side of the heating/cooling seat opposite with respect to the receiving surface.

13. The fluid temperature control device of claim 12, wherein the receiving surface is sloping with respect to an outer surface of the fluid warming/cooling bag when the fluid warming/cooling bag is properly accommodated in the heating/cooling seat.

14. The fluid temperature control device of claim 13, wherein, the first signal is emitted by the first transmitter along an emitted path, the emitted path and the second reflected path are symmetrically arranged with respect to a symmetry axis orthogonal to an outer surface of the fluid warming/cooling bag, and the emitted path and the second reflected path delimit between them an angle between 60° and 120°.

15. The fluid temperature control device of claim 1, wherein an outer surface of the fluid warming/cooling bag is configured to reflect, at least in part, the first signal emitted by the first transmitter, wherein the outer surface is configured to reflect the first signal along a second reflected path, and wherein, when the fluid warming/cooling bag is properly accommodated in the heating/cooling seat, the first receiver intercepts the first signal reflected along the second reflected path.

16. The fluid temperature control device of claim 15, wherein the outer surface of the fluid warming/cooling bag presents a gloss finish.

17. The fluid temperature control device of claim 1, wherein the first transmitter and the first receiver are positioned on a same side with respect to the heating/cooling seat and, when the fluid warming/cooling bag is in the heating/cooling seat, on a same side with respect to the fluid warming/cooling bag.

18. The fluid temperature control device of claim 1, wherein, when the fluid warming/cooling bag is properly accommodated in the heating/cooling seat, the first transmitter and the first receiver are arranged symmetrical with respect to a symmetry axis orthogonal to an outer surface of the fluid warming/cooling bag.

19. The fluid temperature control device of claim 18, wherein, when the fluid warming/cooling bag is properly accommodated in the heating/cooling seat, each of the first transmitter and the first receiver is positioned with an angle with respect to the outer surface of the fluid warming/cooling bag between 30° and 60°.

20. The fluid temperature control device of claim 1, wherein the first transmitter and the first receiver are optoelectronic devices and wherein the first signal is light.

21. The fluid temperature control device of claim 1, wherein the electronic control unit is configured to:
provide an alarm and/or to stop and/or to prevent operation of the fluid temperature control device if the fluid warming/cooling bag is not properly accommodated in the heating/cooling seat; and/or
provide a signal indicating if the fluid warming/cooling bag is properly accommodated in the heating/cooling seat, and/or
provide a signal indicating the type of fluid warming/cooling bag accommodated in the heating/cooling seat.

22. The fluid temperature control device of claim 1, wherein the fluid warming/cooling bag is substantially flat and comprises a main portion delimiting a fluid path with an inlet and an outlet for the fluid.

23. The fluid temperature control device of claim 22, wherein the fluid warming/cooling bag comprises a tab protruding from the main portion, the heating/cooling seat presenting a main seat and a recess for accommodating the tab only when the fluid warming/cooling bag is properly accommodated in the heating/cooling seat, and wherein the tab is configured to reflect the first signal emitted by the first transmitter.

24. The fluid temperature control device of claim 1, wherein the first presence detector is configured to emit the first signal onto an outer surface of the fluid warming/cooling bag of a first type or of a second type only when the fluid warming/cooling bag of the first type or of the second type is properly accommodated in the heating/cooling seat, and wherein the second presence detector is configured to emit the second signal onto an outer surface of the fluid warming/cooling bag of a first type or of a third type only when the fluid warming/cooling bag of the first type or of the third type is properly accommodated in the heating/cooling seat.

25. The fluid temperature control device of claim 24, wherein the first presence detector and the second presence detector are placed side by side.

26. The fluid temperature control device of claim 24, wherein the fluid warming/cooling bag comprises a tab protruding from a main portion of the fluid warming/cooling bag, the heating/cooling seat presenting a main seat and a recess for accommodating the tab only when the fluid warming/cooling bag is properly accommodated in the heating/cooling seat, wherein tabs of the fluid warming/cooling bags of the first, second and third type are different in shape and/or position with respect to the respective main portion, and wherein the tabs of the fluid warming/cooling bas of the first, second and third tape are configured to reflect the first signal and/or second signal.

27. The fluid temperature control device of claim 1, wherein the fluid warming/cooling bag comprises a substantially flat and soft bag insertable through a slot in the heating/cooling seat provided in the fluid temperature control device.

28. Fluid temperature control device for an extracorporeal blood treatment apparatus, comprising:
a casing delimiting a heating/cooling seat configured to accommodate a fluid warming/cooling bag that is configured to be connected to an extracorporeal blood treatment apparatus;
a heating/cooling element operatively active in the heating/cooling seat to heat/cool a fluid warming/cooling bag accommodated in the heating/cooling seat; and
two presence detectors configured to detect if and which type of fluid warming/cooling bag is accommodated in the heating/cooling seat of the fluid temperature control device,
wherein a first presence detector of the two presence detectors is operatively active at the heating/cooling seat and configured to detect the presence of a fluid warming/cooling bag accommodated in the heating/cooling seat,
wherein the first presence detector comprises a first transmitter configured to emit a first signal and a first receiver configured to receive the first signal,
wherein the first receiver is positioned with respect to the first transmitter to selectively receive the first signal emitted by the first transmitter after the first signal is reflected,
wherein a second presence detector of the two presence detectors is operatively active at the heating/cooling seat and configured to detect presence of a fluid warming/cooling bag accommodated in the heating/cooling seat,
wherein the second presence detector comprises a scowl transmitter con wired to emit a second signal and a second receiver configured to receive the second signal,
wherein the second receiver is positioned with respect to the second transmitter to selectively receive the second signal emitted by the second transmitter after the second signal is reflected,
wherein the first presence detector and the second presence detector are placed side by side.

29. The fluid temperature control device of claim 28, comprising an electronic control unit operatively connected to the two presence detectors, the electronic control unit is configured to:

receive detector signals from the two presence detectors,
analyze the received detector signals,
determine, as a function of the analyzed received detector signals, when the fluid warming/cooling bag is properly accommodated in the heating/cooling seat and a type of fluid warming/cooling bag accommodated in the heating/cooling seat.

30. The fluid temperature control device of claim 28, wherein the first and second presence detectors are configured to detect when and which type of fluid warming/cooling bag has been inserted into the blood warming/cooling device.

31. The fluid temperature control device of claim 28, wherein the first and second presence detectors are configured to detect the presence of at least two different types of fluid warming/cooling bags.

32. The fluid temperature control device of claim 28, comprising an electronic control unit operatively connected to said two presence detectors, wherein the electronic control unit is configured to:
receive signals from at least one presence detector of the two presence detectors,
analyze the received signals,
determine, as a function of the analyzed received signals, if the fluid warming/cooling bag is properly accommodated in the heating/cooling seat and a type of fluid warming/cooling bag accommodated in the heating/cooling seat.

33. Fluid temperature control device configured to receive a fluid warming/cooling bag connected to an extracorporeal blood treatment apparatus, the fluid temperature control device comprising:
a casing delimiting a heating/cooling seat configured to accommodate a fluid warming/cooling bag that comprises a main portion delimiting a fluid path with an inlet and an outlet and a tab protruding from the main portion;
heating/cooling elements operatively active in the heating/cooling seat to heat/cool a fluid warming/cooling bag when accommodated in heating/cooling seat;
a presence detector operatively active at the heating/cooling seat to detect presence of a fluid warming/cooling bag accommodated in heating/cooling seat,
wherein the presence detector comprises a transmitter configured to emit a signal and a receiver configured to receive the signal, the transmitter and the receiver being positioned on a same side with respect to the heating/cooling seat and on a same side with respect to the fluid warming/cooling bag when the warming/cooling bag is in the heating/cooling seat;
a receiving surface configured to intercept the signal emitted by the transmitter when the fluid warming/cooling bag is not properly accommodated in the heating/cooling seat, the receiving surface being configured to reflect the signal along a first reflected path, wherein the receiver is spaced from said first reflected path such that the signal reflected along the first reflected path is not captured by the receiver;
wherein the heating/cooling seat comprises a recess configured to accommodate a tab of a fluid warming/cooling bag accommodated in the heating/cooling seat only when a fluid warming/cooling bag is properly accommodated in the heating/cooling seat,
wherein, when a fluid warming/cooling bag is properly accommodated in the heating/cooling seat, the fluid warming/cooling bag is positioned between the transmitter and the receiving surface and the tab is positioned between the transmitter and the receiving surface or covers the receiving surface,
wherein the signal is reflected by the tab.

* * * * *

UNITED STATES PATENT AND TRADEMARK OFFICE
CERTIFICATE OF CORRECTION

PATENT NO. : 11,951,244 B2
APPLICATION NO. : 17/054604
DATED : April 9, 2024
INVENTOR(S) : Michael Jon Wangen Page 1 of 1

It is certified that error appears in the above-identified patent and that said Letters Patent is hereby corrected as shown below:

In the Claims

Column 15, Line 44, 'tint' should read -first-.

Column 15, Line 48, 'bats' should read -bag-.

Column 16, Line 22, 'wherein a receiving surface' should read -wherein the receiving surface-.

Column 16, Line 49, 'wherein the receiving surface' should read -wherein a receiving surface-.

Column 18, Line 17, 'bas' should read -bags-.

Column 18, Line 18, 'third tape' should read -third types-.

Column 18, Line 56, 'scowl transmitter con wired' should read -second transmitter configured-.

Signed and Sealed this
Third Day of June, 2025

Coke Morgan Stewart
*Acting Director of the United States Patent and Trademark Office*